United States Patent [19]

Dickert et al.

[11] Patent Number: 5,614,830
[45] Date of Patent: *Mar. 25, 1997

[54] OIL MONITOR WITH MAGNETIC FIELD

[75] Inventors: Arby D. Dickert, Loudon; James F. Kirkpatrick, Oak Ridge; Eric L. Johnson; Keith A. Hawn, both of Knoxville, all of Tenn.

[73] Assignee: Computational Systems, Inc., Knoxville, Tenn.

[*] Notice: The term of this patent shall not extend beyond the expiration date of Pat. No. 5,262,732.

[21] Appl. No.: 470,279

[22] Filed: Jun. 6, 1995

Related U.S. Application Data

[60] Division of Ser. No. 134,968, Oct. 13, 1993, abandoned, which is a continuation-in-part of Ser. No. 807,041, Dec. 11, 1991, Pat. No. 5,262,732.

[51] Int. Cl.$^6$ ............... G01N 33/28; G01N 27/22; G01N 21/00
[52] U.S. Cl. ............... 324/553; 324/204; 324/674; 73/53.07; 73/61.42; 73/61.72; 340/631; 210/695; 356/70
[58] Field of Search ............... 324/553, 663, 324/674, 676, 678, 681, 686, 361, 204, 227, 228, 232; 73/53.05, 53.07, 61.42, 61.72; 340/627, 631; 210/695; 356/70

[56] References Cited

U.S. PATENT DOCUMENTS

| | | |
|---|---|---|
| 1,940,772 | 12/1933 | Schoenberg . |
| 2,599,583 | 6/1952 | Robinson et al. . |
| 2,889,736 | 6/1959 | Borg . |
| 3,049,964 | 8/1962 | Miller et al. . |
| 3,371,574 | 3/1968 | R. J. Dwyer . |
| 3,790,279 | 2/1974 | Skala . |
| 3,892,485 | 7/1975 | Merritt et al. . |
| 4,003,661 | 1/1977 | Yamano . |
| 4,029,554 | 6/1977 | Ellison . |
| 4,047,814 | 9/1977 | Westcott . |
| 4,302,754 | 11/1981 | Magee et al. . |
| 4,492,261 | 1/1985 | Jones et al. . |
| 4,646,070 | 2/1987 | Yasuhara et al. . |
| 4,677,847 | 7/1987 | Sawatari et al. . |
| 4,692,698 | 9/1987 | Lewis . |
| 4,701,713 | 10/1987 | Eaton et al. . |

(List continued on next page.)

FOREIGN PATENT DOCUMENTS

| | | |
|---|---|---|
| 2165650 | 4/1988 | United Kingdom . |
| 2160655 | 5/1989 | United Kingdom . |

OTHER PUBLICATIONS

B. J. Roylance & A. L. Price, The Development Of A Computer–Aided Systemic Particle Analysis Procedure—CASPA, Dec. 1992 Lubrication Engineering, pp. 940–946.

Tribometrics, Inc. Model 56 Wear Particle Analyzer Tribometrics, Inc. Berkeley, CA. (date unavailable).

Oilcheck; ICC Federated, Racine, Wisc. 53401-1405 (date unavailable).

Analex; Analex Limited; Reading, England. (date unavailable).

Ferro Scan information brochure; Dec. 1990; SENSYS, Ontario, Canada.

*Primary Examiner*—Kenneth A. Wieder
*Assistant Examiner*—Glenn W. Brown
*Attorney, Agent, or Firm*—Luedeka, Neely & Graham, P.C.

[57] ABSTRACT

A method and apparatus for detecting the degree of deterioration in lubricating oil including a grid-like capacitive sensor, that uses the lubricating oil as a dielectric medium, and a magnetic field imposed upon the oil to attract ferromagnetic wear particles into the vicinity of the sensor. Preferably, the magnetic field is generated by a permanent magnet and an electromagnet aligned such that the magnetic field produced by each magnet acts upon the oil along the same axis. A plurality of capacitance measurements are taken at periodic intervals for one type of classification and analysis. Magnetically induced particle concentrations are analyzed visually under the aid of periodic magnetic flux reorientation and optical magnification.

11 Claims, 9 Drawing Sheets

U.S. PATENT DOCUMENTS

| | | |
|---|---|---|
| 4,741,204 | 5/1988 | Luck et al. . |
| 4,791,374 | 12/1988 | Yodice et al. . |
| 4,796,204 | 1/1989 | Inoue . |
| 4,831,362 | 5/1989 | Tsaprazis . |
| 4,857,829 | 8/1989 | Sagae et al. . |
| 5,179,346 | 1/1993 | McGee et al. ............... 324/693 |
| 5,262,732 | 11/1993 | Dickert et al. ............... 324/672 |
| 5,360,039 | 11/1994 | Verrilli ............... 210/695 X |
| 5,506,501 | 4/1996 | Fogel et al. ............... 324/204 |

OIL MONITOR WITH MAGNETIC FIELD

This application is a division of application Ser. No. 08/134,968 filed Oct. 13, 1993 and now abandoned, said Ser. No. 08/134,968 being a Continuation-In-Part of application Ser. No. 07/807,041 filed Dec. 11, 1991 and issued on Nov. 16, 1993 as U.S. Pat. No. 5,262,732.

BACKGROUND OF THE INVENTION

1. Field of the Invention

This invention relates to an apparatus for detecting the degree of deterioration of lubricating oil and, more particularly, to such an apparatus detecting deterioration due to the following: corrosive products caused by such conditions as oxidation, nitration, and the formation of acids; oil insoluble contaminants such as water and glycol coolants; and ferromagnetic particles caused by system wear.

2. Description of the Prior Art

The presence of corrosive products, oil insoluble contaminants or ferromagnetic particles in a lubricating oil can create a threat to the system in which the oil is used because of the unnecessary wear and damage that can occur to the system if the oil is not promptly changed.

Many methods and devices have been developed to detect the contamination or breakdown of oil. One such device, shown in U.S. Pat. No. 4,646,070 issued to Yasubara, discloses a device for detecting deterioration in lubricating oil which comprises a pair of capacitor electrodes positioned in the lubricating oil. The device uses the oil as a dielectric between the sensors to develop a frequency voltage signal across the sensor capacitor, thus determining the dielectric and deterioration of the oil. A major drawback of this device and others is that they do not inform the tester of the specific type or magnitude of deterioration in the system.

The preferred embodiment of the present invention allows simultaneous testing and identification of corrosive products, contamination, and ferromagnetic wear particles. Thus, since the apparatus detects the type of products present in the oil, a user is able to make a more knowledgeable determination of the conditions causing the deterioration of the oil. Furthermore, the device provides this determination much more economically than laboratory testing. The device also allows multiple tests of the same oil sample because it does not consume the sample during the testing process. Preferably, the device allows testing of the oil outside the system in which the oil is used, thereby allowing the oils of many different systems to be tested by the same device.

SUMMARY OF THE INVENTION

The present invention provides an apparatus for monitoring the condition of lubricating oil preferably for the possible presence of corrosive products, contamination such as water, and ferromagnetic metals in the oil. The apparatus includes containing means for holding the lubricating oil, magnet means for inducing a magnetic field upon the lubricating oil, sensor means for determining a physical property of the oil in the presence of a magnetic field and optical magnifying means to assist visual analysis of debris separated from the oil.

Preferably, the magnet means includes a permanent magnet, an electromagnet and a switching means for changing the polarity of the electromagnet. Thus, both the permanent magnet and the electromagnet simultaneously impose their magnetic fields upon the lubricating oil attracting any ferromagnetic particles in the oil. Furthermore, in the preferred embodiment, the magnetic field of the electromagnet changes polarity over time, alternately reinforcing and canceling the permanent magnetic field, thereby vibrating and reorienting the ferromagnetic particles with the change in the electromagnet's flux orientation without repulsing the particles away from the sensor.

The sensor means preferably includes a sensor, a means for monitoring the output of the sensor, and a means for processing the sensor's output. The apparatus is assembled in a manner allowing the contained oil to be exposed to the sensor, and the sensor has at least two conductors for which the oil provides an insulating dielectric medium. Thus, the sensor acts as a capacitor and its capacitance varies in relation to at least the area of the conductors, the distance between the conductors, and the dielectric constant and other properties of the oil. This relationship between the sensor and the lubricating oil allows the determination of the properties of the oil as it is influenced by the magnetic field.

In the preferred embodiment, the processing means of the invention determines the amount and type of deterioration in the oil by comparing the capacitance of the sensor when exposed to a test oil sample to the capacitance of the sensor when exposed to a pure calibration sample of the type of oil tested. A higher capacitance in the test oil (relative to the calibration oil) that remains relatively constant over time indicates the presence of corrosive products. A steady increase of the sensor's capacitance while exposed to the test oil indicates the presence of contamination in the oil. A fluctuating increase of the sensor's capacitance while exposed to the test oil indicates the presence of ferromagnetic particles in the oil. The changing polarity of the electromagnet causes the ferromagnetic particles to reorient thereby fluctuating the increase of the sensor's capacitance.

The invention takes advantage of the characteristic differences between oil and its contaminants. Oil, for example, has a lower density than most contaminants, including water. As a result, gravity is likely to draw the contaminants to the sensor. Also, most contaminants possess electrical characteristics that differ widely from those of oil. Lastly, many contaminants have a magnetic response. Oils normally do not have a magnetic response. Such differences make it possible for the invention to discriminate between oil and virtually every likely contaminant.

Further details and advantages of this apparatus will become more apparent in the following description and the accompanying drawings.

BRIEF DESCRIPTION OF THE DRAWINGS

The present invention may best be understood by reference to the Detailed Description of a preferred embodiment when considered in conjunction with the Drawings in which.

DETAILED DESCRIPTION OF THE PREFERRED EMBODIMENT

Figure 1:
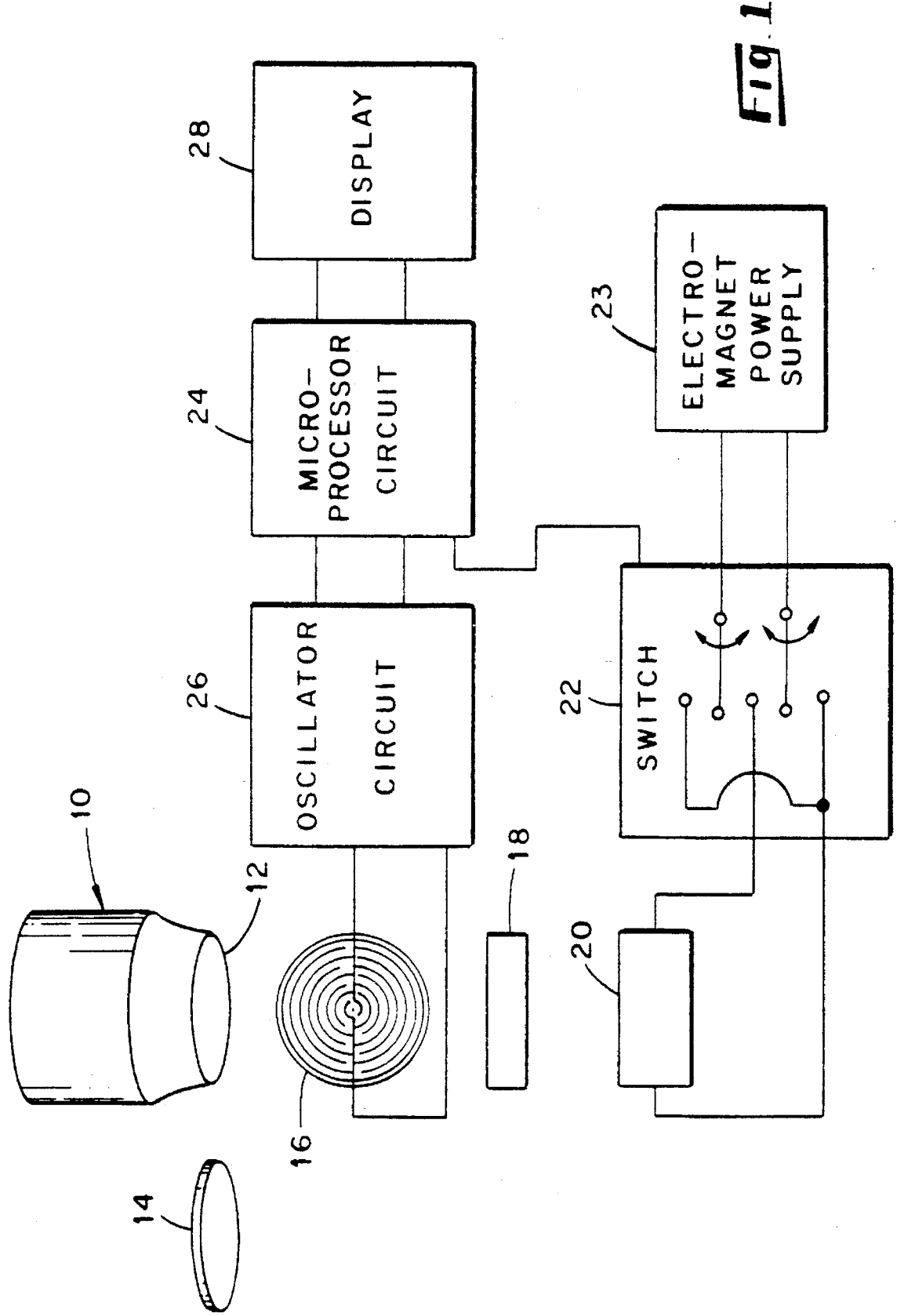
FIG. 1 is a diagrammatical block diagram of a preferred embodiment of the Oil Monitor.

Referring now to the drawings wherein the representations depict the preferred embodiment, there is shown in FIG. 1 a container 10 for holding the sample of lubricating oil that is to be tested. The container has an open mouth 12 and a removable and resealable lid 14 for sealably attaching over the mouth 12. For testing the oil, the container 10 is placed in a measurement position which preferably entails orienting the container 10 vertically with the mouth 12 situated downward so that the mouth 12 covers a horizontally placed sensor 16 thereby allowing the oil to flow down into welled contact with the sensor 16. The measurement position further allows gravity to influence the oil held in the container 10 thereby causing any contaminants in the oil to migrate toward the sensor 16.

In FIG. 1, the sensor 16 is symbolically represented and is shown removed from the mouth 12 for clarity of illustration. It will be understood that the sensor 16 seals against the mouth 12 to close the container 10 and contain the oil.

A permanent magnet 18 is placed vertically beneath the sensor 16 to allow the magnetic field produced by the permanent magnet 18 to attract any ferromagnetic particles in the oil toward the sensor 16. An electromagnet 20 is located vertically beneath the permanent magnet 18 to allow the magnetic field produced by the electromagnet 20 to act in conjunction or opposition to the permanent magnet 18 depending on the polarity of the electromagnet 20. The electromagnet 20 is electrically connected to switch 22 which is in turn electrically connected to an electromagnet voltage supply 23. The switch 22 and the electromagnet voltage supply 23 allow the electromagnet to be turned on in a north-south orientation, turned on in a south-north orientation, or turned off. The switch 22 in the preferred embodiment is electrically connected to a microprocessor circuit 24 which controls the change in the polarity of the electromagnet 20 as well as the rate at which the electromagnet 20 is turned on and off, which is preferably about one (1) cycle per second. In this embodiment, the electromagnet 20 is a model EMR75 manufactured by Miami Magnet Company operating at 12 volts and about 750 milliamps. The permanent magnet 18 has a diameter of one inch, a thickness of one quarter (¼) inch and a strength that about matches electromagnet 20.

The sensor 16 is electrically connected to an oscillator circuit 26 which uses the sensor 16 as a capacitor to generate an output signal at a frequency corresponding to the capacitance. The oscillator circuit 26 is electrically connected to the microprocessor circuit 24 which uses the generated signal frequency to determine the presence and magnitude of corrosive products, contamination, and ferromagnetic particles in the oil. The microprocessor 24 is electrically connected to the display 28 which outputs the results of the microprocessor's determinations.

Figure 2:
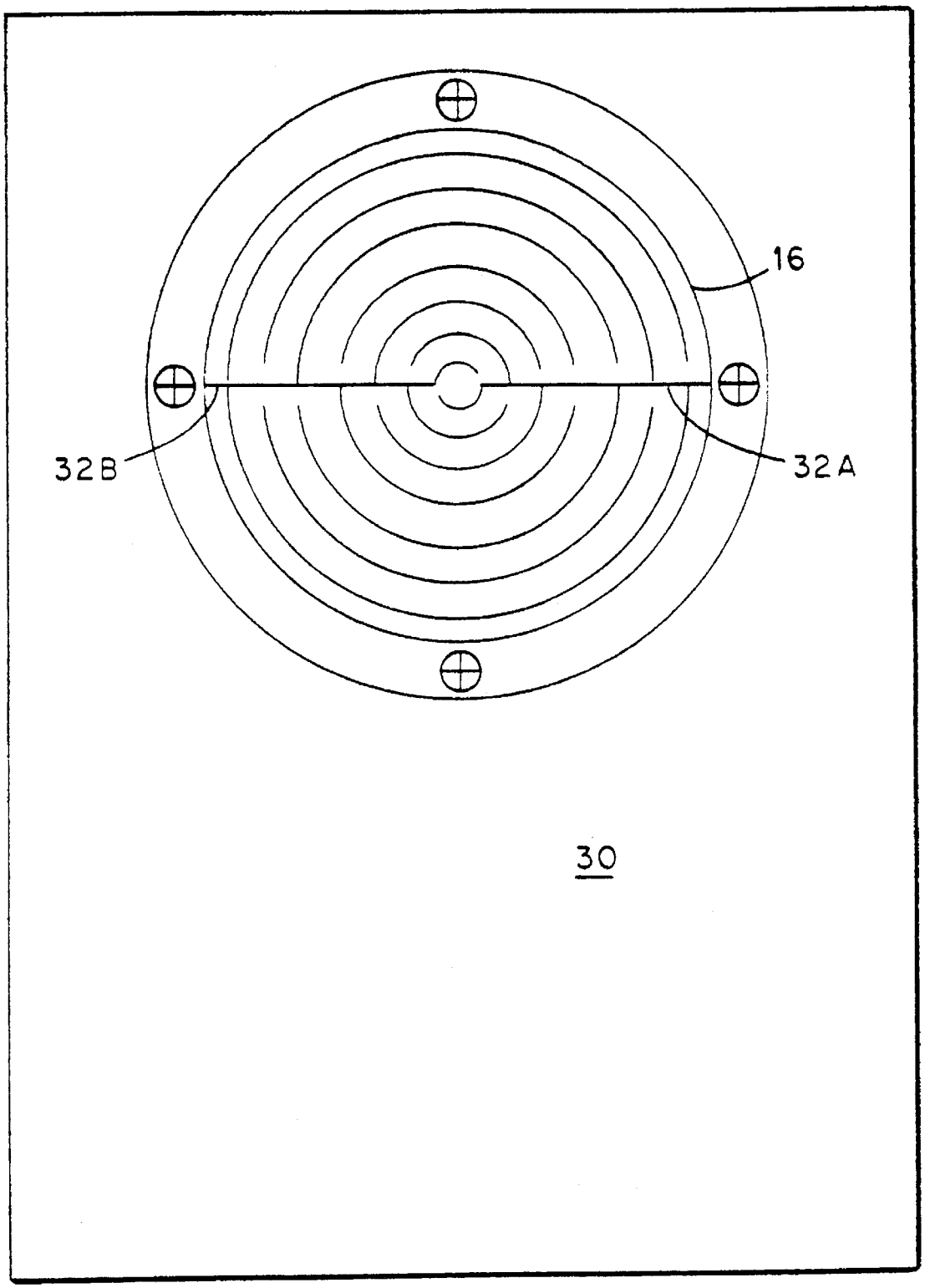
FIG. 2 is a plan view of the Oil Monitor showing the sensor.

FIG. 2 depicts an enlarged, somewhat diagrammatic, top view of the preferred embodiment of the sensor 16 as mounted to the test box 30 which also contains the permanent magnet 18, the electromagnet 20, the switch 22, the electromagnet voltage supply 23, and the oscillator circuit 26 of FIG. 1. The preferred sensor 16 is constructed in a open grid-like formation and is formed from two conductors 32a and 32b having extensions forming concentric half circles. The oil which flows into and adjacent to the sensor acts as the insulating dielectric medium between the conductors 32a and 32b. Thus, the conductors 32a and 32b act as capacitor plates with the capacitance varying with, at least, the area of the conductors 32a and 32b, the distance between the conductors 32a and 32b, and the dielectric constant of the oil. Numerous capacitance type sensors could be used, but in this embodiment, the sensor has a diameter of about one inch; the conductors 32a and 32b have a diameter of about 250 microns and are spaced apart a distance of about 250 microns; and the sensor 16 has a capacitance in air of about 30 picofarads.

Figure 3:
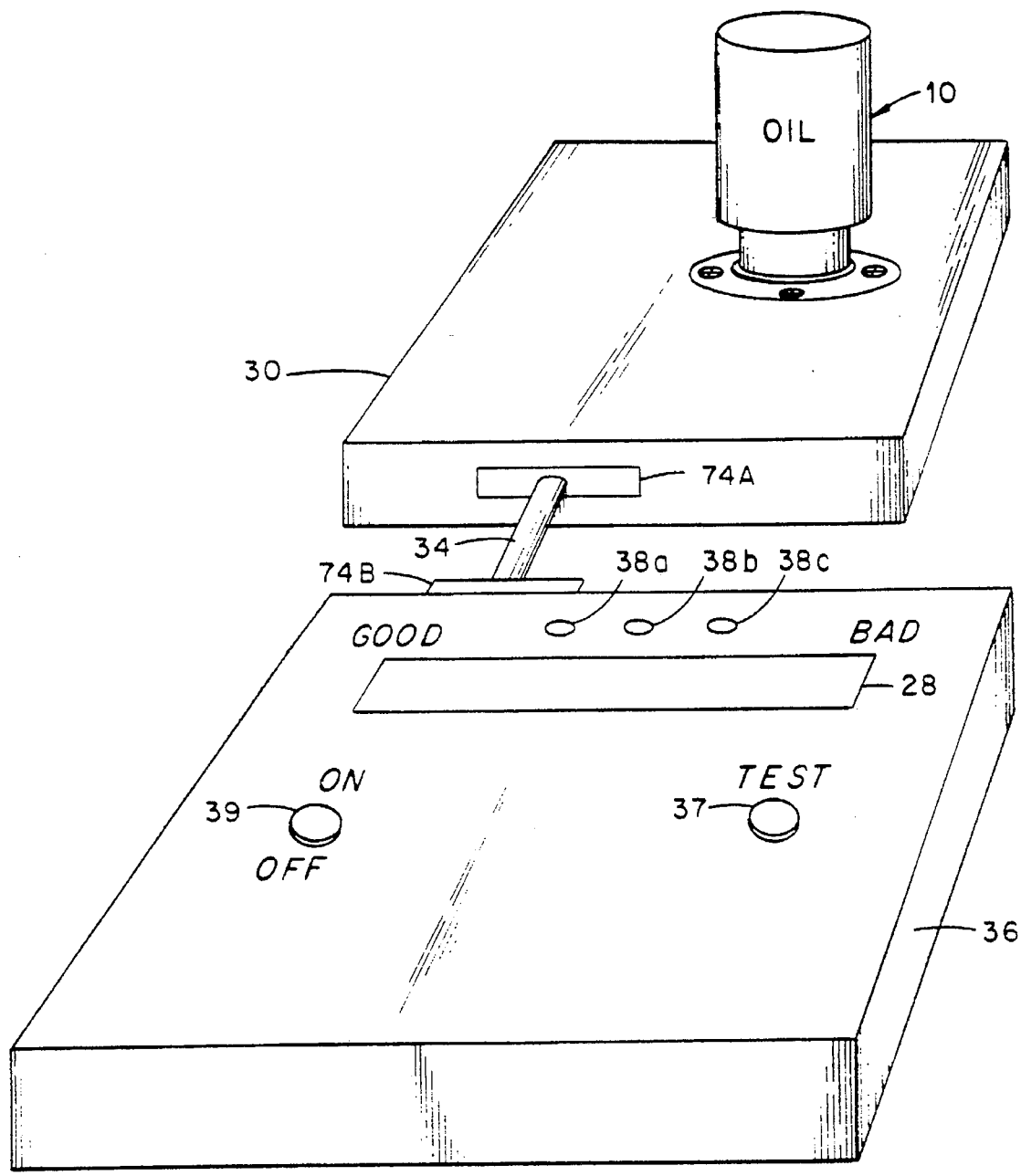
FIG. 3 is a somewhat diagrammatic perspective view of the Oil Monitor.

FIG. 3 depicts an external, somewhat diagrammatic, view of the preferred embodiment of the apparatus. The container 10 is shown in the measurement position on the test box 30. A shielded serial cable 34 electrically connects the components in the test box 30 at connector port 74a to those components in the display box 36 by means of connector port 74b. The display box 36 encloses the microprocessor 24 of FIG. 1. The display 28 is preferably an LCD for displaying the value of contamination, corrosion and ferromagnetic particle levels. The display 28 is mounted on the display box 36 and is electrically connected to the microprocessor 24 within the box. Further depicted are three LEDs, 38a, 38b and 38c, that are electrically connected to the microprocessor 24 within the display box 36 and energized corresponding to the changing levels of corrosion, contamination or ferromagnetic particles.

Figure 4:
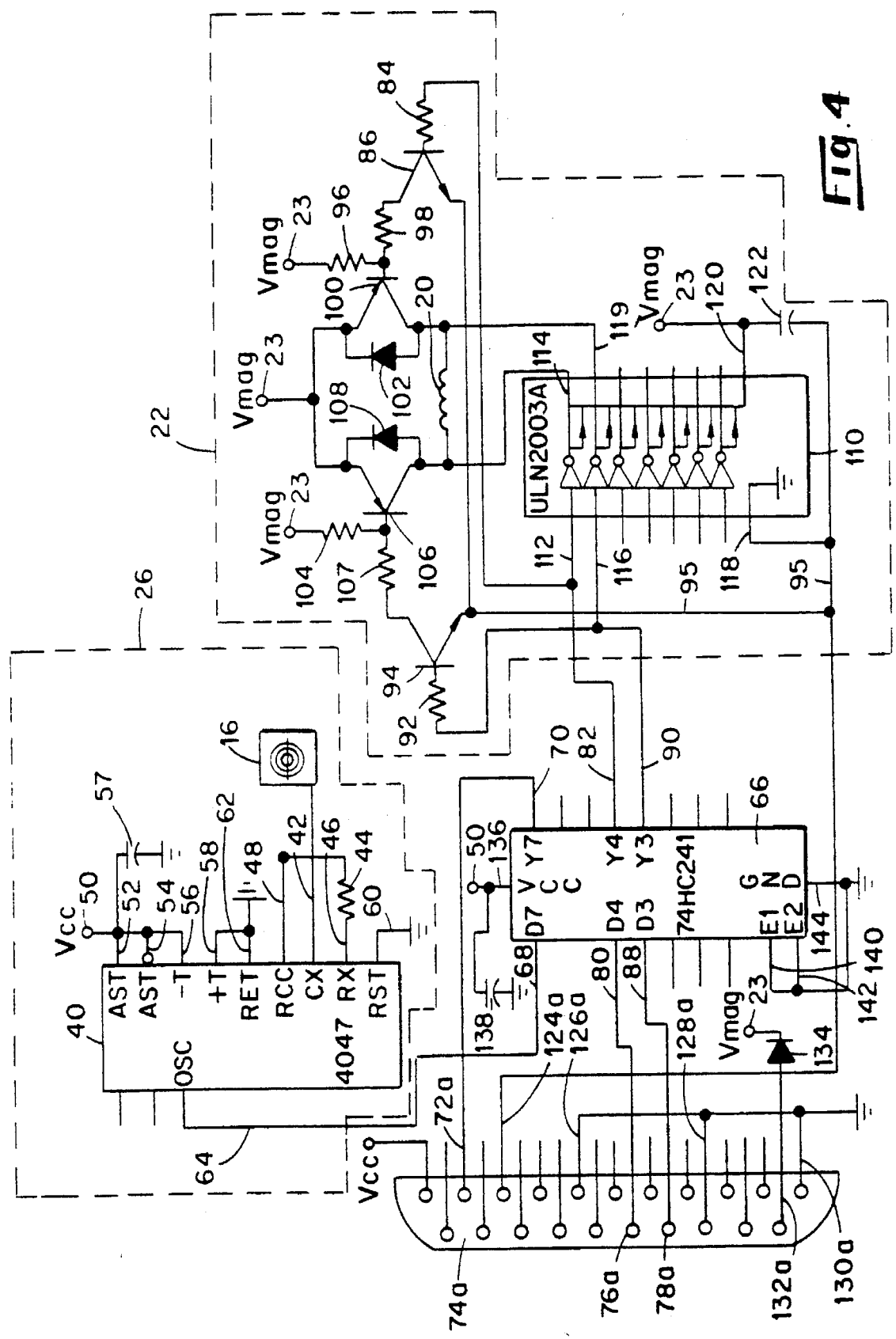
FIG. 4 is a circuit diagram of the sensor and associated analog circuit.

FIG. 4 depicts the preferred embodiment of the internal circuitry of the test box 30 shown in FIG. 3. The oscillator circuit 26 performs the function of generating a frequency pulse based upon the capacitance of the sensor 16. The oil in the sensor 16 acts as the dielectric medium, thereby altering the capacitance of the sensor. The capacitance increases as the dielectric increases (see Formula 1) causing an overall decrease in the frequency produced by the oscillator circuit 26. The presence of polar oxides in the oil causes an increase in the dielectric constant. Additionally, since water has a higher dielectric content than oil, its presence in the oil will cause an increase in the dielectric constant of the oil as the water settles into the vicinity of the sensor 16. If a substantial quantity of water accumulates on the sensor 16, it can cause the sensor 16 to be shorted. The presence of ferromagnetic particles in the oil also causes an increase in the capacitance of the sensor 16 because the accumulation in particles on the sensor increases the sensor's surface area and capacitance in accordance with Formula 1.

$$C = k*E*(A/d)$$  Formula 1:

where: C=the capacitance of the sensor 16; k=the dielectric constant of the oil in the sensor 16; A=the surface area of the sensor 16; and, d=the distance between the sections of the sensor.

The sensor 16 is connected to a pin 42 of a monostable multivibrator 40 and is connected in parallel with the resistor 44 to pin 46 and pin 48 of the monostable multivibrator 40. A constant voltage source 50 is connected to pins 52, 54 and 56 of the monostable multivibrator 40 while pins 58, 60 and 62 are grounded. Pins 52, 54 and 56 are also connected to ground through a, preferably, 0.1 microfarad capacitor 57. Thus, sensor 16 is connected in an R-C circuit to determine the frequency of the signal (pulses) from pin 64. The preferred monostable multivibrator is a general CMOS logic chip Model 4047.

The pin 64 which carries the oscillator signal pulses is connected to a pin 68 of a non-inverting buffer chip 66 which isolates the signal and outputs it from pin 70. The pin 70 is connected to a pin 72a of a connector port 74a. A signal is thereby sent through the connector port 74a along the serial cable 34 of FIG. 3 to an identical connector port 74b of the display box 36 of FIG. 3.

The connector port 74a also receives signals from the microprocessor 24 from pins 76a and 78a of the connector port 74a. These signals control the switch 22 for changing the polarity of the electromagnet 20 and for turning the electromagnet 20 on or off. As the permanent magnet 18 continuously attracts ferromagnetic particles onto the surface of the sensor 16, when the electromagnet, when turned on in opposition to the permanent magnet 18, will cause the particles on the sensor to shift thereby changing the surface area of the sensor which results in an altered frequency output from the monostable multivibrator 40. Thus, the electromagnet will cause a fluctuation in output pulses as its polarity is changed if ferromagnetic particles are present in the oil. In the preferred embodiment, an electromagnet is employed for shifting the ferromagnetic particles in the vicinity of the sensor, but it will be understood by those of ordinary skill in the art that a similar effect could be produced by a movable permanent magnet that could be shifted or rotated to change the magnetic field. Furthermore, in the preferred embodiment, the electromagnet's polarity is reversed to produce the maximum fluctuation while continuously attracting particles with the permanent magnet 18. Persons knowledgeable in the art will further understand that total reversal of the polarity of the electromagnet is not required.

The pin 76a of connector port 74a is connected to a pin 80 of the buffer chip 66 which isolates the switching signal and outputs it from pin 82. The pin 82 is connected in series with a resistor 84 to the base of an NPN transistor 86. The pin 78a of connector port 74a is connected to pin 88 of the buffer chip 66 which isolates the signal and outputs it from the pin 90. The pin 90 is connected in series with a resistor 92 to the base of an NPN transistor 94. The emitters of the transistors 86 and 94 are tied together and attached to a signal ground wire 95 which acts to reduce noise in the system. The collector of transistor 86 is connected in series through resistors 96 and 98 to the electromagnet power supply 23, which provides $V_{mag}$, and further connected through resistor 98 to the base of a PNP transistor 100. A diode 102 is coupled across the emitter and collector of transistor 100 thus acting as a protection device for transient relief. The emitter of transistor 100 is further connected to the electromagnet voltage supply 23, and the collector of transistor 106 is further coupled to the electromagnet 20. The collector of transistor 94 is connected in series to the electromagnet power supply 23 through resistors 104 and 107 and is further connected to the base of a PNP transistor 106 through resistor 107. A diode 108 is coupled across the emitter and collector of transistor 106 thus acting as a protection device for transient relief. The emitter of transistor 106 is further connected to the electromagnet voltage supply 23 (preferably a battery), and the collector of transistor 106 is further connected to the electromagnet 20.

The pin 82 of the buffer chip 66 is also coupled with a pin 112 of a Darlington driver chip 110 which operates as a current sink, dependent upon the logic level, and is connected from pin 114 to the electromagnet 20 in conjunction with the collector of transistor 106. The pin 90 of buffer chip 66 is connected to a pin 116 of the driver chip 110 which is in turn coupled from pin 118 to the electromagnet 20 in conjunction with the collector of the transistor 100. This configuration allows the current flow to the electromagnet 20 to be alternated or shut off completely by the microprocessor 24 thus providing the switch 22.

The driver chip 110 is connected to the signal ground wire 95 through a pin 118 and is connected to the electromagnet voltage supply 23 through a pin 120 which is further coupled through a series capacitor 122 to the signal ground wire. The signal ground wire 95 is connected to pin 124a of the connector port 74a.

The connector port 74a has pins 126a, 128a, and 130a connected to ground and has pin 132a connected through a diode 134 to the electromagnet power supply 23.

The buffer chip 66 has pin 136 connected to the constant voltage source 50 which is in turn coupled to ground through capacitor 138. The buffer chip also has pins 140, 142 and 144 coupled to ground.

Figure 5:
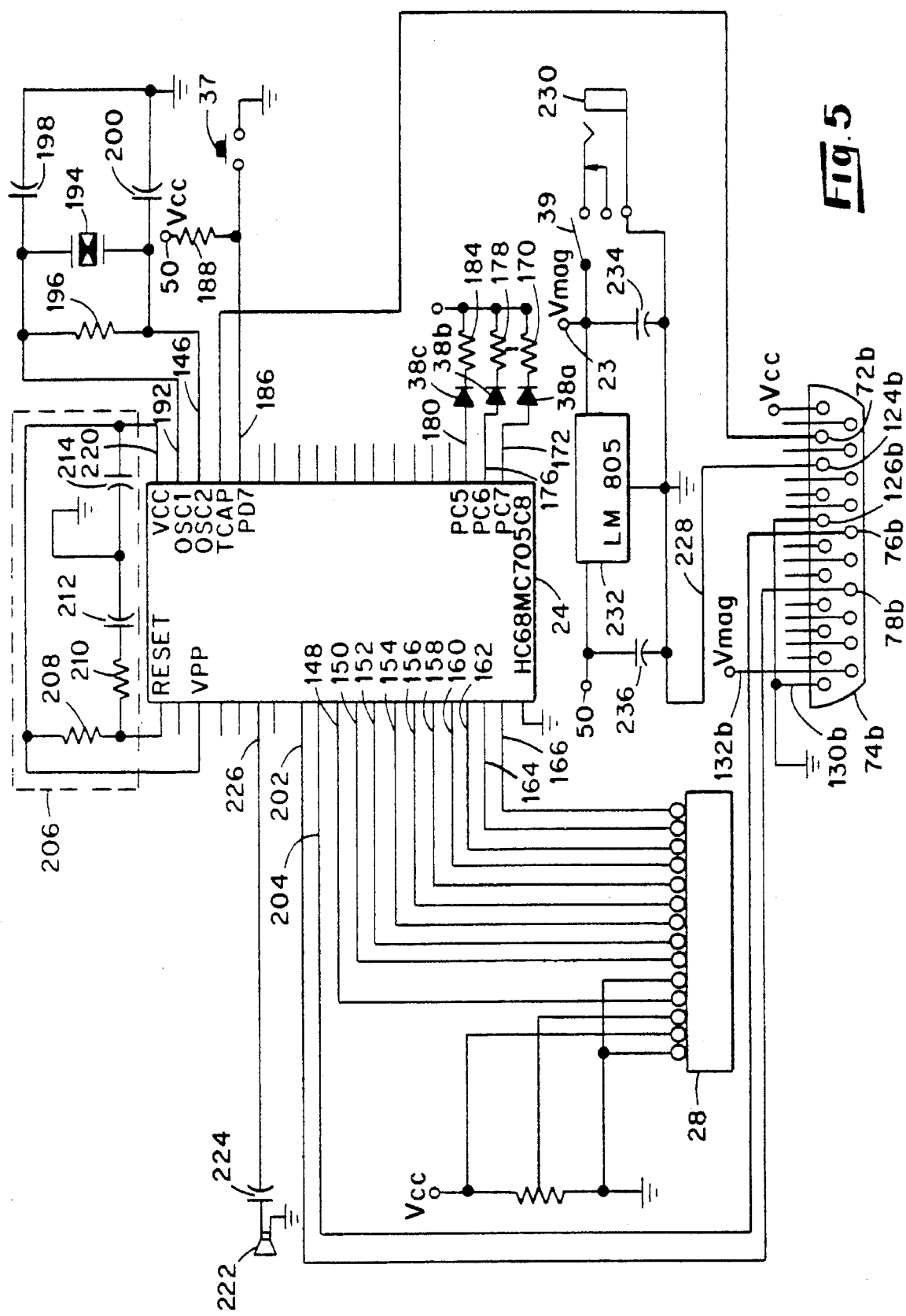
FIG. 5 is a circuit diagram of the microprocessor and associated circuitry that monitors the sensor and produces an output.

FIG. 5 depicts the internal circuitry of the display box 36 of FIG. 3. The connector port 74b connects the test box 30 to the shielded serial cable 34. The pin 72b carries the oscillator pulse and is connected to the microprocessor 24 at pin 146. The preferred microprocessor is an HCMoss microcontroller unit model MC68HC705C8 with erasable programmable read only memory. The microprocessor 24 counts the frequency pulses produced by the multivibrator 40 to determine the amount of contamination, corrosive products and ferromagnetic particles in the test oil.

A fresh, petroleum-based lubricating oil is primarily composed of hydrocarbon molecules with no net electrical charge and which are weakly polar or have a non-polar charge distribution. Fresh mineral oils can be characterized as having a very high electrical resistance and a relatively low dielectric constant (permittivity). These electrical properties change as the oil degrades and becomes contaminated. Specifically, increases in insoluble content, the presence of moisture and acids, or the presence of conductive metallic debris will increase the dielectric constant of an oil, or reduce its resistance, or both.

A combined measure of permittivity and resistivity can be made by measuring the AC impedance or effective capacitance (rate of charge over applied potential) across two plates separated by a quantity of oil. An approximate model for the system is an ideal capacitor influenced primarily by permittivity and a parallel resistance primarily influenced by ionic conduction. Charge mobility not involving conductive particles in a dielectric fluid involves mechanical motion of charged or dipole particles in the fluid. Therefore, system impedance is tied to the parameters which describe the hydrodynamics of particles moving in a fluid. These parameters include the temperature-dependent oil viscosity, the applied (electrical) forces, particle size, and particle shape. As might be expected, increasing molecular size and/or increasing viscosity damps particle response to electrical force, resulting in a decrease in the frequency at which the maximum effective capacitance is achieved. Consequently, sample readings of absolute instantaneous permittivity and loss performed with a conventional dielectrictrometer will provide a limited amount of information about the bulk oil chemistry.

The strength of the present invention is based on measuring the time-rate-of-change of effective capacitance in the presence of time-varying magnetic and electric fields over a standard test period, 500 seconds, for example. These applied fields act along with gravity to draw ferromagnetic particles, polar insolubles, and conductive metal particles down onto the sensor 16. Consequently, the time-rate-of-change values are specifically related to the amount and species of contaminates which are extracted from the oil rather than to the general, bulk oil properties.

The invention uniquely identifies ferromagnetic debris by comparing the time-rate-of-change in a magnet off state to the time-rate-of-change in the magnet states. In addition, the instrument also reads the absolute effective capacitance at the beginning of the test. This value can be used to compare the test oil to a sample of the fresh bulk oil when the results of the fresh oil calibration test have been stored. The comparison provides a non-specific indication of changes in the bulk oil chemistry. In the absence of a calibration sample, this value should still be tended over time to detect sudden changes in bulk oil chemistry which typically accompany additive depletion or gross contamination.

Figure 6:
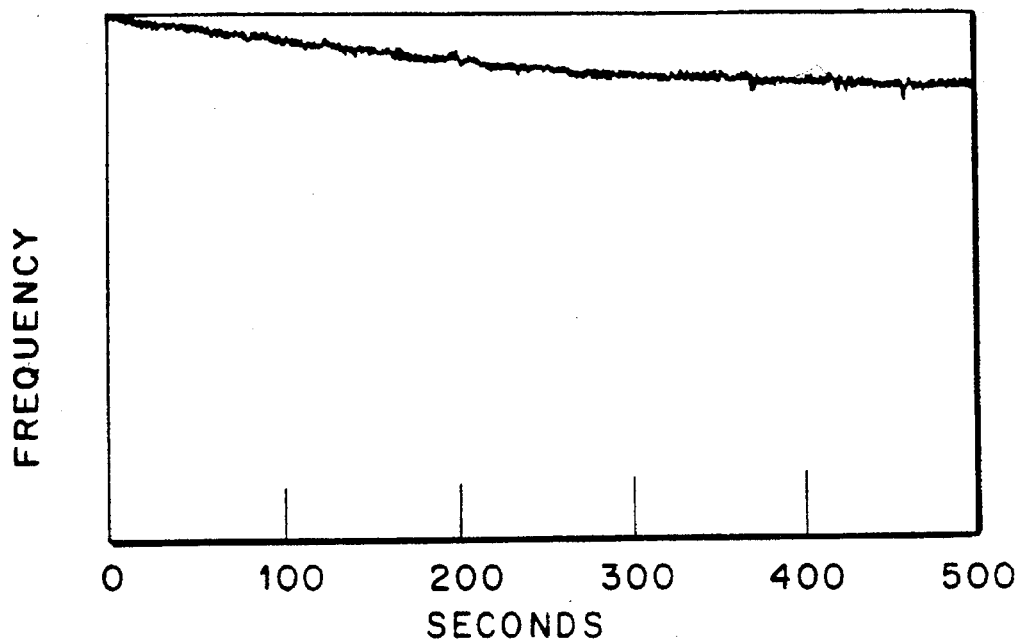
FIG. 6 is a graph of frequency vs time data taken by the invention from uncontaminated lubricating oil.

FIG. 6 illustrates how the invention "sees" a fresh oil. The broad curve across the top of the plot represents sequential frequency readings of an oscillating circuit which decreases with the increases in effective system capacitance. The plot is smooth with very little downward slope indicating that there was little change in the effective capacitance during the test. We know, therefore, that the contaminant population is small and benign. There are no diverging curves for the magnet on states.

Figure 7:
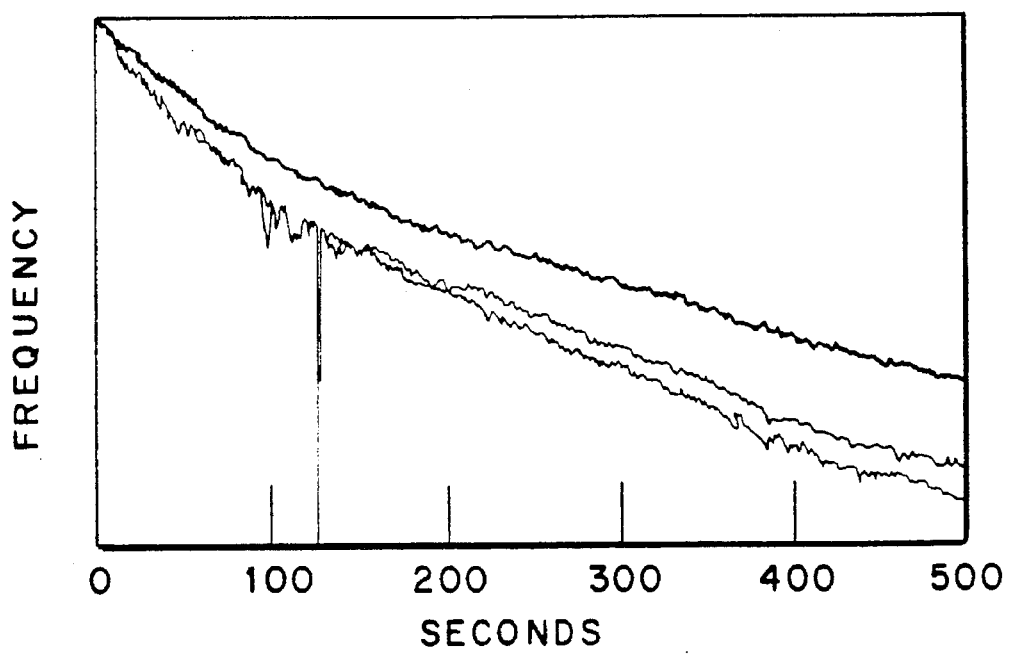
FIG. 7 is a graph of frequency vs time data taken by the invention from lubricating oil used in a pump having significant use and wear.

FIG. 7 illustrates how the instrument "sees" the same pump oil after it has been in service in a pump experiencing significant wear. Note the much steeper downward slope and the increasing separation of the magnet on states (two lower curves) from the upper magnet off state curve. This separation is the indication of ferrous debris. Also note that in this case the magnet on curves have a jagged and spiked profile at about 120 seconds into the test when relatively large magnetic particle(s) were forced onto the sensor, while the magnet off curve is relatively smooth.

Figure 8:
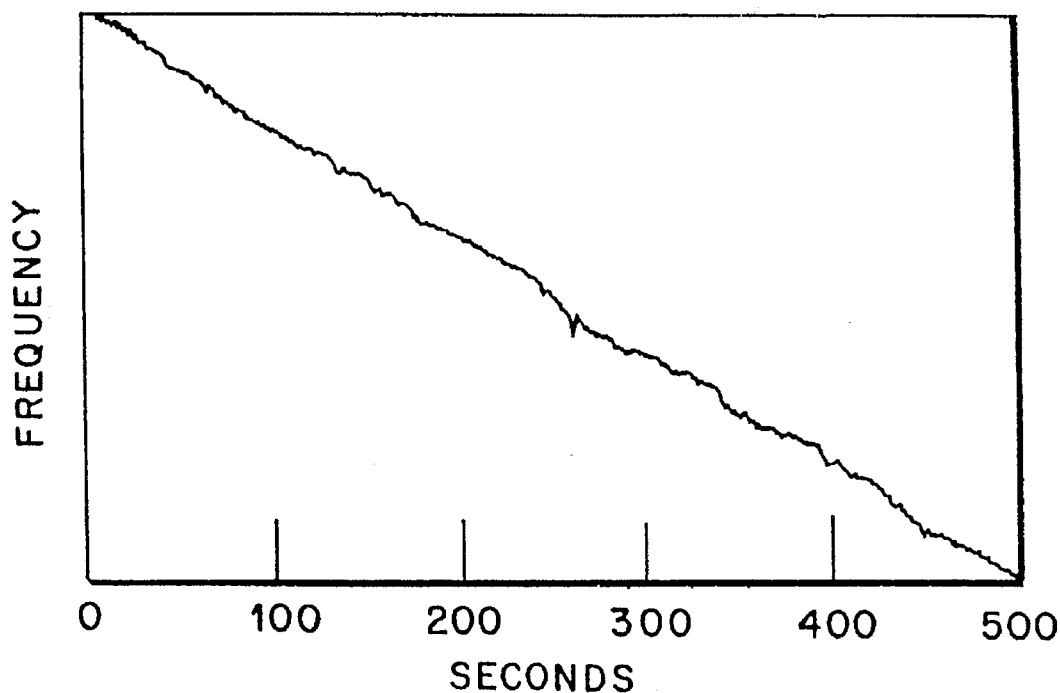
FIG. 8 is a graph of frequency vs time data taken by the invention from lubricating oil used in a turbine having approximately 0.13% water entrained thereon.

FIG. 8 illustrates how a turbine oil with roughly 1300 ppm (0.13%) water appears to the instrument. There is a steep and nearly linear downward slope indicating that the contaminate is being primarily drawn onto the grid by gravity rather than by the magnetic fields with their spatial gradient. This is confirmed by the fact that there is also no divergence of the magnet on curves from the magnet off curves. Also note the perturbation in the curve at about 260 seconds caused by a droplet of "free" water contacting the grid as opposed to finely dispersed moisture.

Upon initial application of power to the microprocessor 24, the microprocessor 24 is set in calibration mode whereby it stores certain calibration counts for use in the test mode. The calibration mode stores certain values which will be used as the "normal" values for the oil to be tested. These values are obtained from running the calibration sequence upon an unused sample of the oil. The calibration sequence is similar to the test sequence. To perform the calibration sequence, the calibration oil is put into the container 10, and the container is placed in measurement position.

The microprocessor then begins receiving and counting the pulses output from the monostable multivibrator 40. Pulse counts are made when the electromagnet is turned on in north-south polarity, turned on in south-north polarity, and turned off. In the preferred embodiment, these three count readings constitute one cycle.

The mean calibration value, $M_c$, is determined over a number of cycles, preferably, twenty cycles, and, preferably, the first ten of which are counted and ignored. During each cycle between ten and twenty cycles, the pulse count is stored while the electromagnet is off, and the mean value of the stored pulse counts is stored as $M_c$. The number of cycles used to determine $M_c$ is a matter of design choice, but it is preferred to ignore the first few cycles and then determine an average based on a number measurements taken over a number of cycles.

After the twenty-first cycle, the pulse count when the electromagnet is off is stored as the magnet-off calibration value $OFF_c$. Furthermore, the difference between the electromagnet when off and when on in north-south polarity is stored $N_c$ and the difference between the electromagnet when off and when on in south-north polarity is stored $S_c$. After these calibration values are stored, the microprocessor 24 reconfigures and resets its internal flags for test mode. Since the values obtained in the calibration mode are used as the "normal" values for the oil, a poor calibration oil will cause the test sequence to produce improper results.

The test mode is run by filling the container 10 with the test oil and placing the container in measurement position. The microprocessor 24 then begins running test cycles. After twenty cycles (preferably) have been run in the test mode, the microprocessor 24 stores the mean pulse count obtained between the tenth and the twentieth cycles (preferably) when the electromagnet is turned off as the mean test value $M_T$. This mean value $M_T$ is substracted from the similarly obtained calibration value $M_c$ and the difference is output to the LCD display 28 as the Corrosion Index R.

$$R = M_c - M_T \qquad \text{Formula 2}$$

Thus, if the test oil contains no corrosion, the mean values obtained in the test and calibration mode will be approximately the same, giving a Corrosion Index R of zero.

This index is a measure of changes in bulk oil chemistry. An increase in this index indicates that the oil is increasingly able to support electrical conduction owing to the presence of polar molecules, moisture, or suspended, charge-bearing particulate. These conditions typically lead to increased wear and corrosion. The most common causes of an increase in this index include thermally accelerated oxidation and nitration, the formation of acids from combustion blow-by in engines, and increased moisture content.

After the twenty-first cycle (preferably), the microprocessor 24 substracts the pulse count taken when the electromagnet is turned off (the magnet-off test value $OFF_T$) from the mean test value $M_T$, and the difference between the magnet-off calibration value $OFF_c$ and the mean calibration value $M_c$ is further substracted. The resultant value is output to the LCD 28 as the Contamination Index C.

$$C = (M_T - OFF_T) - (M_c - OFF_c) \qquad \text{Formula 3}$$

This index is a measure of the level of oil-insoluble contaminants in the oil as opposed to changes in the bulk oil chemistry. Some common contaminants include water, glycol coolants, metallic wear debris, large insoluble by-products of combustion, and abrasive solids such as road dust. The contamination index value is updated similarly each cycle using the magnet off test value $OFF_T$ for each cycle. This method of determining the contamination allows any pulse offsets due to corrosion to be disregarded. Furthermore, the testing for contamination during each cycle allows for the time that it takes for gravity to draw the contaminants into the vicinity of the sensor 16.

Figure 9:
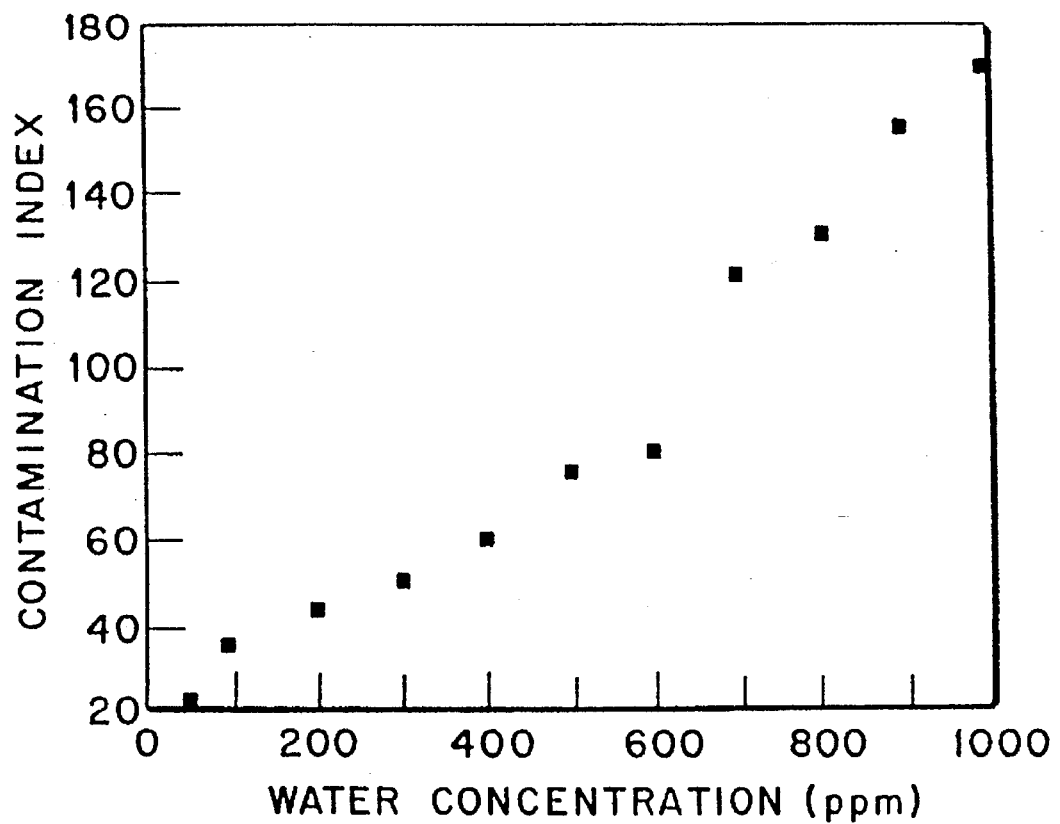
FIG. 9 is a representative graph of the invention Contamination Index vs Water Content.

FIG. 9 is a plot of the Contamination Index for a series of test samples prepared by introducing known amounts of water into a fresh turbine oil. Again, note the linear relationship between the test data and the known concentrations. The instrument is capable of detecting water at concentrations as low as 100 ppm by weight in light oils. It should be noted that the contamination index is sensitive to the conductivity of a contaminant as well as its concentration. In practice this means that it will assign a higher value to highly corrosive salt water than it will to less damaging clean water. In either case the instrument will detect "free" water as opposed to finely dispersed water.

Beginning at the twenty-first cycle, the difference between the pulse count when the electromagnet 20 is off and the pulse count when the electromagnet 20 is on is determined. This determination is made for the difference when the electromagnet is in both polarities and stored as $N_T$ and $S_T$. Similar values obtained from the calibration mode are then substracted from the test mode values with the resultant values outputted to the LCD 28 as the Ferromagnetic debris Index $F_x$.

$$F_x = (N_c - N_t) + (S_c - S_c) \qquad \text{Formula 4}$$

This index is sensitive to conductive, ferromagnetic particles. It increases with particle size, surface conductivity, and debris concentration. The index is primarily sensitive to recent, severe wear of oil-wetted steel and iron parts. This index increases with ferrous wear debris concentration and size.

Similar values may be obtained in succeeding cycles and added to the previous value so that a running total is obtained and displayed.

$$F_{TOT} = F_x + F_{x1} \qquad \text{Formula 5}$$

Thus, the amount of ferromagnetic debris in the oil is indicated.

Figure 10:
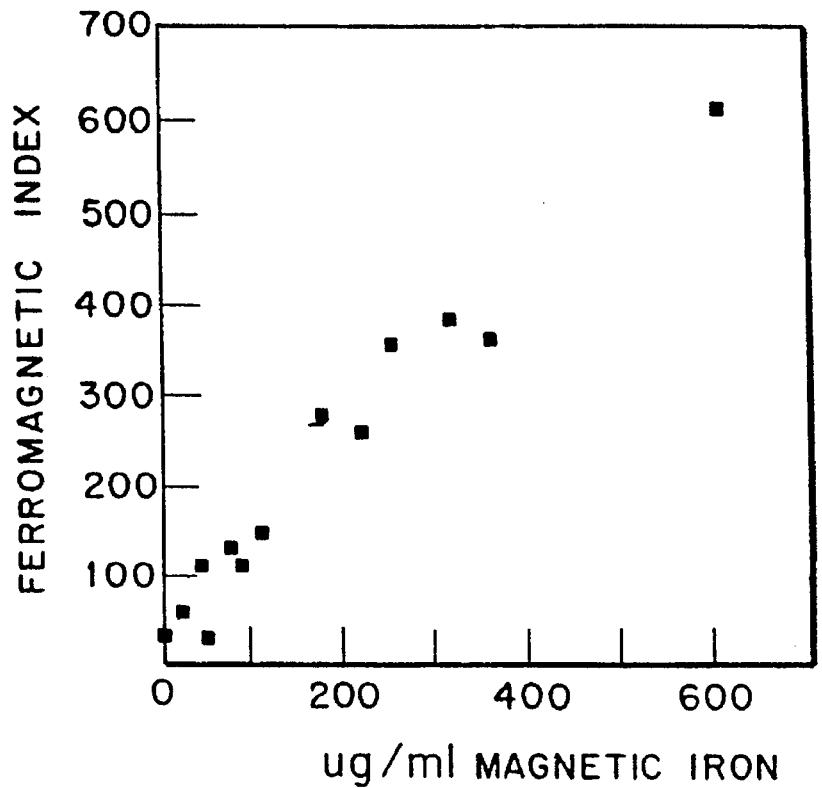
FIG. 10 is a graph of the invention Ferromagnetic Index vs Iron Content.
Figure 12:
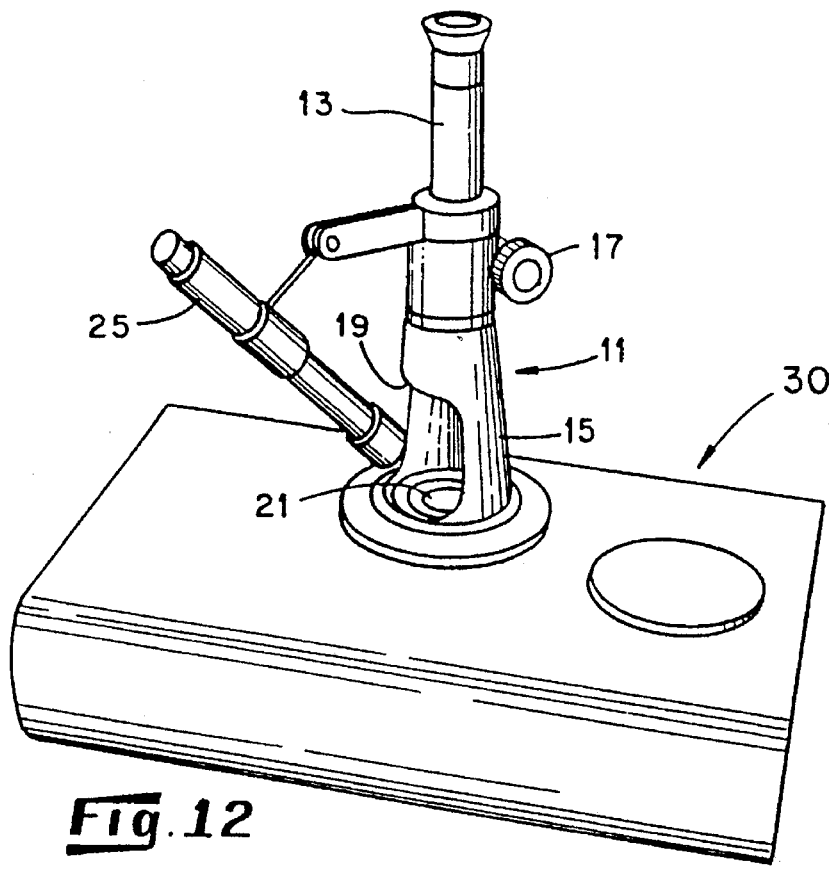
FIG. 12 illustrates an expanded use embodiment of the invention.

FIG. 10 is a plot of the Ferromagnetic Index from a series of tests conducted with a fresh turbine oil contaminated with varying known amounts of 4 to 6 micron iron particles. Note the linear relationship between known content and the index. The instrument will detect iron debris concentrations as low 1 μg/ml.

It should also be noted that this index is sensitive to particle size as well as particle concentrations. For a given concentration this index will increase with particle size. This size sensitivity aids in detecting the large particles produced by abnormal (as opposed to normal) wear.

Another useful index value from the invention is the "OilLife Index"™, OL. This index value is the product of an algorithm which reflects the combined effect of oil degradation and contamination, i.e. when the oil is no longer suitable for continued use due to oxidation or acidity or the presence of corrosive fluids such as glycol or water or the presence of conductive particles. This OilLife Index™ relies upon a 500 cycle data base wherein the median of the last five (496–500 cycle) magnet-off oil calibration values CAL are reduced by the median of the last five (496–500 cycles) magnet-off oil test values TES and the sensor noise value NOS. This summation is divided by a suitable constant, C.

$$\text{Formula 6: } OL = \frac{CAL - TES - NOS}{C}$$

Figure 11:
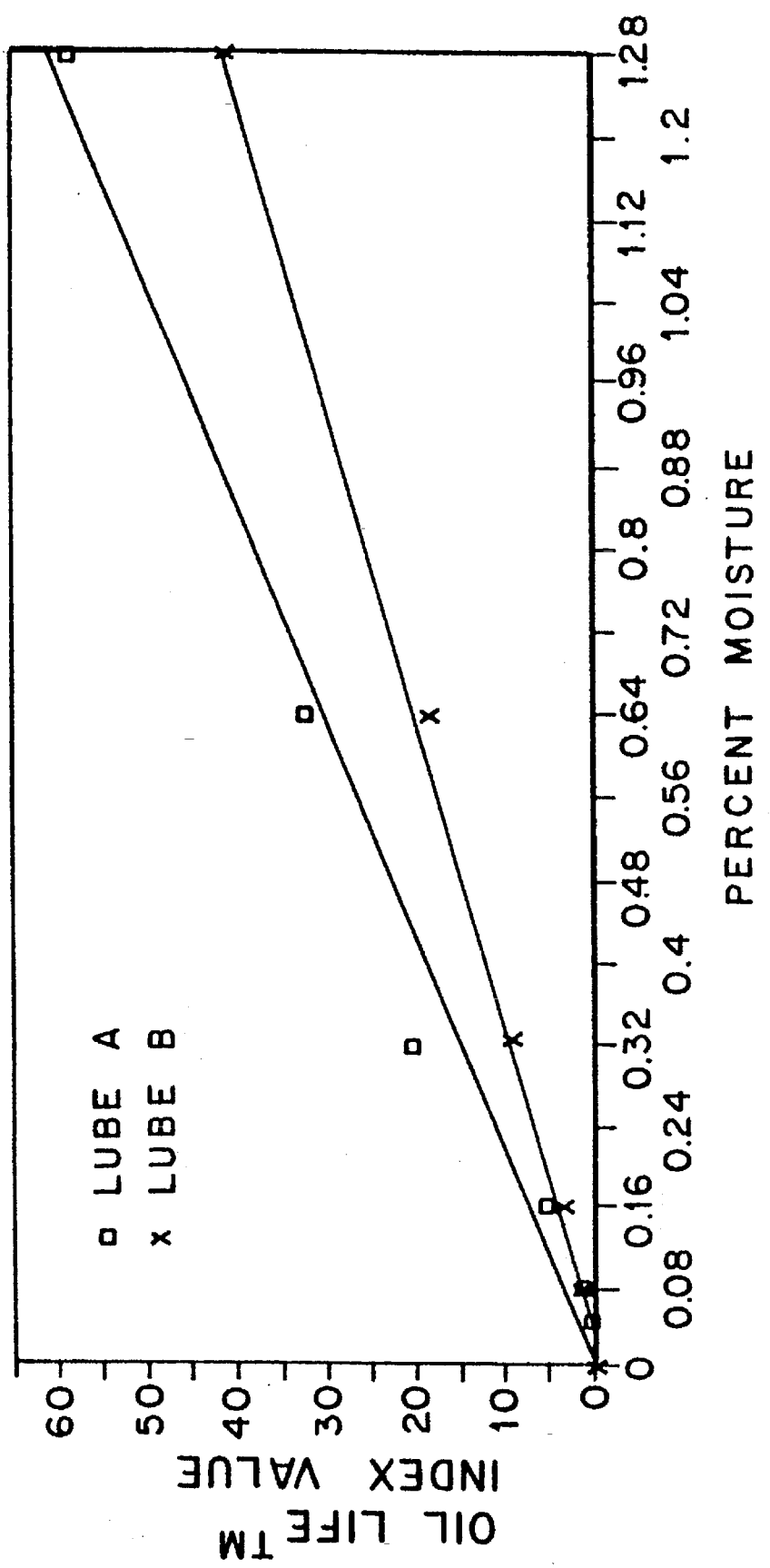
FIG. 11 is a graph of the invention OilLife Index™ vs. percentage of water entrained in lubrication oil.

FIG. 11 graphs the OilLife Index™ value determination respective to percentage of moisture content contaminating two synthetic compressor lubricants. Note will be taken of the Index data linearity on both lubricant examples.

The microprocessor 24 uses pins 148, 150, 152, 154, 156, 158, 160, 162, 164 and 166 to output the index values to the display 28. In the preferred embodiment, LEDs are used as a further indicator of the condition of the oil. The microprocessor 24 sends a signal to a green LED 38a, which is tied to the constant voltage source 50 through a resistor 170. The signal is sent from pin 172 thereby energizing the green LED 38a. If the Corrosion Index, the Contamination Index, the Ferromagnetic debris Index or the OilLife Index™ increases to a significant level, the green LED 38a is de-energized and the yellow LED 38b is energized by a signal from pin 176 of the microprocessor 24 to indicate the need for caution because of a borderline oil sample. The yellow LED 38b is connected to the constant voltage source 50 through a resistor 178. If any of the index values increase to a "high" reading (determined by the designer according to the anticipated application of the device), the yellow LED 38b is de-energized and the microprocessor sends a signal through a pin 180 to energize a red LED 38c, which is connected to the constant voltage source 50 through a resistor 184, to thereby indicate that the oil sample is "bad." In the event that a pulse count reading produced by the sensor for any condition of electromagnet 20 drops to a level that would indicate a shorting of the sensor due to large amounts of water or debris, the red LED 38c will be pulsed and the word "CRITICAL" will be sent to the display 28.

In the preferred embodiment, the microprocessor 24 receives the pulse counts for 100 cycles and then stops if the Contamination index and the Ferromagnetic debris index values remain very small. However, if the Contamination or Ferromagnetic debris indicates an appreciable amount of deterioration in the oil, the microprocessor continues receiving for 500 cycles to determine the full amount of the contaminants. The word "FINISHED" will be sent to the display 28 when the microprocessor 24 completes its readings.

The microprocessor checks for a high reading on pin 186 to determine if the test should be aborted. Aborting occurs by pressing the test button while in test mode. The pin 186 is connected to the constant voltage source 50 through a resistor 188 and to the test button 37 which connects to ground when pressed, thereby allowing the line to be driven high.

The microprocessor controls the polarity and the power to the electromagnet 20 by output signals from pins 202 and 204 which are connected to pins 76b and 78b of the connector port 74b. Thus, the signals are transferred along the shielded serial cable 34 to the connector port 74a of the test box 30. A low signal generated on both pins 202 and 204 will force the electromagnet 20 into its "off" mode. A high signal generated upon pin 202, while a low signal is generated on 204, will force the electromagnet into the "on" mode in north-south polarity. Finally, a high signal generated upon pin 204, while a low signal is generated on pin 202, will force the electromagnet into the "on" mode in south-north polarity.

A reset circuit 206 including resistors 208 and 210 connected to capacitors 212 and 214 is attached to the constant voltage source 50 and acts to pull up the input voltage to five volts after the supply contact is made. The reset circuit 206 is attached to pins 216, 218 and 220 of the microprocessor 24, thereby assuring that the internal reset of the microprocessor is working properly.

In the preferred embodiment, a beeper alarm 222 is used for signaling the presence of dangerous levels of deterioration and contamination in the test oil. The beeper 222 is attached through a capacitor 224 to a pin 226 of the microprocessor 24.

The connector port 74b has a pin 124b connected to a probe ground wire 228 which is connected to a power clip 230 for hook up to an external power source. The switch 39 engages the external power source when depressed thereby powering the electromagnet voltage supply 23. The switch 39 is further connected to a voltage regulator 232 which regulates the voltage to five volts for supplying the constant voltage source 50 which powers the digital requirements of the system. The electromagnet voltage supply 23 is connected to the probe ground wire 228 through resistor 234, and the constant voltage source 50 is similarly connected to the ground wire 228 through resistor 236.

The connector port 74b has pins 126b and 130b connected to ground. The connector port 74b further has pin 132b connected to the electromagnet voltage supply 23.

At the conclusion of a foregoing test sequence, the accumulated debris and wear particles may be viewed directly for analysis and direct interpretation for type and origin. FIG. 11 illustrates a suitable viewing apparatus for this purpose which comprises a microscope 11 having an optics tube 13 that is axially slidable within an open bottom support base 15. Focal adjustment of the optic tube is made by rotation of the adjustment knob 17. A wall opening 19 in the support base 15 permits the microscope viewing area 21 at the bottom of base 15 to be illuminated by a lamp such as battery powered penlight 25. The support base bottom is sized to cover or fit in or over the sensor 16 so as to place the contaminant deposition surface of the sensor 16 in the microscope viewing area 21.

Reversing the procedure for connectively sealing the sample container 10 to the sensor 16, the unit is gently inverted from the test position to drain the oil sample away from the container mouth 12 interface with the sensor 16. This inverting process is carried out with such care as to avoid disruption of the contaminant deposition pattern on the sensor 16. Oil surface tension and presence of the permanent magnet 18 field is normally sufficient to secure the contaminant pattern during a careful inversion.

With the oil sample fluids drained from the container 10 mouth opening 12, the seal between the container and the sensor may be separated and the container 10 confined sample fluids removed from the sensor 16 unit leaving the accumulated deposits of contaminant particles exposed openly on the sensor deposition surface.

Without flushing the contaminant deposits from the sensor 16 surface or otherwise disrupting the deposition pattern, the sensor 16 is re-erected and the microscope 11 positioned with the base 15 placed over or connected to the sensor 16 whereby the sensor surface plane coincides with the microscope 11 viewing area 21. In this condition and disposition, the contaminant particle deposition patterns and organization may be visually scrutinized and analyzed under different lighting and stimulation conditions.

For example, the deposits may be viewed under the illumination of spectrally restricted light such as violet, red or yellow. Similarly, an optic tube 13 eyepiece filter may be positioned to accomplish similar results. Additionally, a camera may be connected to the optic tube to photograph the deposits on video tape or spectrally specific film. Moreover, in this exposed disposition, the electromagnet 20 may be actuated to stimulate movement of the magnetically responsive particles thereby revealing their unique classification patterns which conform to the permanent magnet flux lines. In the presently preferred embodiment of the invention, these flux lines are revealed in two or three concentric circles of clustered magnetic material deposited on the sensor 16 surface. These magnetically responsive and geometrically distributed particles will physically move in alternating unison to the magnetic field pole reversals. Randomly distributed non-magnetic material has no response to the presence or absence of the alternating magnetic field.

Using a 100× power microscope, this technique has been used to observe particles as small as 1.0 microns. Without the microscope, but with the electromagnetic motion enhancement, only particles larger than about 40 microns may be directly observed.

This visual information may reveal the extent of damage occurring to a machine as well as the cause. Most wear particles in a lubricant result from three root causes: adhesive wear, abrasive wear or metal fatigue.

Adhesive wear is that which results from sliding, scuffing, or rubbing contact between surfaces. Sliding type adhesive wear is common and quite normal wear which takes place for most applications. Scuffing and rubbing are not normal.

Normal adhesive wear generates very small (0.1 to 5 microns) wear particles as high spots are sheared down. Abnormal adhesion (result of scuffing or rubbing) may generate much larger particles.

Abrasive wear is the cutting action normally caused as hard particles gouge out long (10 to several 100 microns) and sometimes curled strips of metal. Sand or metal wear particles are frequently the cause of abrasive wear. Abrasive wear particles get broken into smaller pieces as they are milled by the gears.

Fatigue (also called "high cycle fatigue") occurs when the metal surfaces fail due to repeated cyclic loading. This is commonly seen on gear teeth and rolling element bearings.

Fatigue particles tend to be relatively large (10 to 20 microns) having blocky or spherical shape. The presence of spherical particles usually is a very strong indication of fatigue failure. These particles are generated when subsurface cracks allow a chunk of material to break free which then rolls around. When the surface connected cracks join to release a blocky surface particle, the sub-surface spherical particles are released.

In a different mode of analysis, oil contamination deposits on the sensor surface may be transferred from the original accumulation surface to a separate, analyzing surface having, for example, greater electromagnetic field strength or complex illumination or light filter capacities. In this analysis mode, the deposits are bodily transferred in their originally deposited organization by means of a blotter or slide supported adhesive gel. By foregoing the capacitance measuring function of the invention, the deposition surface of the sensor 16 may be covered with a transfer sheet such as a filter paper or transparent film as a direct deposition surface to lift the contaminant specimen bodily intact from the sensor 16 with a minimum of magnetic classification disturbance.

Given these enhanced visual insights into the cause of wear particles in the oil as isolated by the invention, the maintenance and operations personnel may choose and pursue the correct follow up actions. For instance, after detecting abrasive wear particles, the oil and filter should be changed. Seals and air filters should be inspected to determine how sand or dirt might be getting into the tube system.

Similar logical actions can be derived for the other forms of wear.

Direct visual observation of mechanical wear particles makes it easy for equipment maintenance people to "see" what is taking place in the lubricated system. A magnified 100× view of wear particles and other debris makes it much easier to solve root causes of lube system problems.

Although a preferred embodiment is described herein, it will be understood that the invention is capable of numerous modifications, rearrangements and substitutions of parts without departing from the scope of the invention as defined in the following claims. For example, particular oil borne contaminants have substantially unique, frequency dependent dielectric properties that may be identified by incremental or sweep variations in the sensor 16 input signal frequency. Useful data may also be acquired by measuring the phase shift of a sensor 16 signal in the microwave frequency range.

As our invention, we claim:

1. A method of appraising the presence of contaminants suspended within a sample of lubrication oil, said method comprising the steps of:

supporting a stagnant quantity of sample oil by a capacitance responsive surface in direct interface therewith to receive deposits of gravity biased fluids and particles suspended within said sample;

imposing a magnetic field upon said oil sample that is oriented to induce movement of magnetically responsive particles suspended within said sample toward said responsive surface;

measuring and reporting the capacitive response of said surface to gravity and magnetically induced settlement of suspended particles thereupon for a measured time period.

2. A method of appraising contaminants in oil as described by claim 1 wherein said magnetic field comprises a steady state component and an alternating magnetic flux pattern component.

3. A method of appraising contaminants in oil as described in claim 1 wherein the capacitive response of said surface is measured and reported at a plurality of substantially uniform time intervals within said time period.

4. A method of appraising contaminants in oil as described by claim 1 wherein the capacitive response of said surface to an uncontaminated sample of said oil is measured and recorded for archived comparison.

5. A method of appraising contaminants in oil as described by claim 1 wherein said capacitance responsive surface is stimulated by a variable frequency oscillator signal.

6. A method of appraising contaminants in oil as described by claim 5 wherein capacitive responses of said surface to settlement of particles thereon changes the stimulation frequency of said oscillator signal.

7. A method of appraising contaminants in oil as described by claim 1 wherein said quantity of sample oil is removed from direct interface with said surface in the presence of at least said steady state magnetic field component at the end of said measured time period.

8. A method of appraising contaminants in oil as described by claim 7 comprising a visual evaluation of particles accumulated on said surface under the influence of an alternating magnetic flux pattern.

9. A method of appraising contaminants in oil as described by claim 8 comprising the enhancement of said visual evaluation with optical magnifying means.

10. A method of appraising contaminants in oil as described by claim 7 comprising removal of said particles from said surface to a microscope viewing field for visual evaluation.

11. A method of appraising contaminants in oil as described by claim 10 wherein said microscope viewing field is influenced by an alternating magnetic flux pattern.

* * * * *